United States Patent [19]

Rockliffe et al.

[11] Patent Number: 4,471,871

[45] Date of Patent: Sep. 18, 1984

[54] PACKAGED DRY-TO-THE-TOUCH ARTICLE AND METHOD OF PACKAGING THE ARTICLE

[75] Inventors: Jeffrey W. Rockliffe, South Wirral; Edward G. Smith, Wirral, both of England

[73] Assignee: Lever Brothers Company, New York, N.Y.

[21] Appl. No.: 444,635

[22] Filed: Nov. 26, 1982

[30] Foreign Application Priority Data

Dec. 2, 1981 [GB] United Kingdom ............... 8136347
Dec. 2, 1981 [GB] United Kingdom ............... 8136318
Dec. 2, 1981 [GB] United Kingdom ............... 8136317

[51] Int. Cl.³ .................... B65D 85/00; B65D 85/70
[52] U.S. Cl. .................................. 206/205; 206/210; 206/361; 206/484; 53/396; 428/35; 428/74; 428/194; 428/905; 428/913
[58] Field of Search ............... 206/205, 210, 438, 484, 206/361; 428/35, 68, 74, 75, 76, 166, 194, 474.4, 532, 905, 913; 53/396

[56] References Cited

U.S. PATENT DOCUMENTS

| 4,007,258 | 2/1977 | Cohen et al. | 424/22 |
|---|---|---|---|
| 4,230,687 | 10/1980 | Sair et al. | 424/22 |
| 4,277,024 | 7/1981 | Spector | 428/905 |
| 4,309,469 | 1/1982 | Varona | 428/74 |
| 4,337,862 | 7/1982 | Suter | 428/35 |

OTHER PUBLICATIONS

"Textile Research Journal" 44, No. 3, pp. 165-173 (1974), (H.-D. Weigmann et al).
"Makromoleculare Chemie", vol. 9, No. 239, Sep., 1953, pp. 254-260 (H. Staudinger et al).
"Chemical Abstracts", vol. 82, No. 7, Mar. 31, 1975, No. 84759H, Dtsch. Lebens M.-Rundsch., 1974, 70 (10), 349-351 (H. G. Maier).
"Chemical Abstracts", vol. 79, No. 23, Dec. 10, 1973, No. 135486q; Lebens M.-Wiss. Technol., 1973, 6 (4), 147-150, (F. Osman-Ismail et al).

Primary Examiner—William J. Van Balen
Attorney, Agent, or Firm—Milton L. Honig; James J. Farrell

[57] ABSTRACT

A substantially dry-to-the-touch article contained in a closed, moisture impervious container, comprises a matrix of polysaccharide and/or protein and a non-aqueous liquid having a dielectric constant of from 1.5 to 40 included within the matrix. The article although apparently dry is capable of releasing the included non-aqueous liquid when contacted with water. The article can form a sheet or wad of fabric or it can be presented in the form of a tablet or powder.

14 Claims, No Drawings

PACKAGED DRY-TO-THE-TOUCH ARTICLE AND METHOD OF PACKAGING THE ARTICLE

The invention relates to packaged articles, particularly articles, such as fabrics and powders comprising a polymer matrix containing an included non-aqueous liquid which is releasable when the article is contacted with water. The invention is more particularly directed to dry-to-the-touch polysaccharide-based or protein-based articles, contained within a closed, moisture impervious container, which have utility in the delivery of the included non-aqueous liquid, as and when desired, when the article is moistened with water, to provide any of a variety of functions such as cleansing, deodorising or odorising of surfaces or enclosed spaces, or in the flavouring of foods.

The manufacture of articles, particularly disposable fabric articles such as paper tissues, cleansing cloths and pads and sanitary towels, and powdered products such as abrasive cleaners or talc for absorbing or removing superficial body fluids from the skin or spillages of fluid from other surfaces, is a well established industry. Such articles can be dry, in which case they rely on their absorbency to mop up body fluids and spillages. Alternatively, they can be pre-moistened with alcohol or other suitable solvent, often together with perfume, so that in use, delivery of the solvent can facilitate degreasing and deodorising of the surface to which they are applied. Moist articles of this type are usually packaged individually in a foil pouch or other closed container in order to prevent evaporation of the solvent.

Clearly there has long existed a need for an article which is dry-to-the-touch, which is simply packaged, and which possesses the ability to deliver a solvent or perfume or other active liquid material as and when required to the point of use. It is with the provision of just such a packaged article that the invention is concerned.

It has been proposed by Weigmann and Ribnick in "Textile Research Journal", 44, No 3, pages 165–173 (1974), to treat textile yarns such as rayon with a series of solvents in sequence to entrap within the yarn a solvent such as carbon tetrachloride whose removal is resistant to drying. Weigmann et al reported that the mechanism of entrapment was connected with the re-forming of hydrogen bonds between cellulose chains after replacement of a hydrogen bond breaking solvent with a non-polar solvent which itself cannot break hydrogen bonds. They also observed that cellulose hydrogen bonds could be re-opened by introducing water to liberate the trapped solvent molecules. These observations by Weigmann et al resulted from a study on behalf of the textile industry of the effect of solvents on the mechanical properties and the dye diffusion characteristics of textile yarns.

We have now discovered that it is possible to treat an article consisting essentially of cellulose or other polymers, by a solvent exchange procedure to obtain a dry-to-the-touch article which is capable of delivering, when moistened with water, a non-aqueous liquid having a specific utility at the point of use.

Accordingly, the invention provides a substantially dry-to-the-touch article contained in a closed, moisture impervious container, the article comprising:

(i) a matrix of polysaccharide or protein or a mixture thereof; and (ii) a non-aqueous liquid, having a dielectric constant of from 1.5 to 40, included within the matrix;

the weight ratio of the non-aqueous liquid to the matrix being from 1:1000 to 1:1; the non-aqueous liquid being included in the matrix in such a manner that it is releasable when the article is contacted with water.

It should be explained that by "substantially dry-to-the-touch article", we mean that the article does not feel moist when handled, nor does it exude liquid when squeezed.

It should also be explained that by "included" we mean that the non-aqueous liquid is physically entrapped within the matrix of polysaccharide and/or protein, and that its release can be triggered on contacting the article with water or water vapour.

The matrix of the article according to the invention comprises polysaccharide, protein or a mixture thereof, which polymers possess a degree of hydrogen bonding sufficient to include the non-aqueous liquid until opening of the hydrogen bonds to release the non-aqueous liquid is achieved by contacting the article with water.

When the matrix comprises polysaccharide, the preferred polysaccharides are chosen from celluloses and starches. When the matrix comprises protein, the preferred proteins are chosen from keratin and casein.

When the matrix comprises a cellulose, it can be derived from native cellulose such as that derived from cotton, flax, wood or other plants, or it can be regenerated cellulose such as viscose rayon. It is also possible to employ a chemically modified cellulose provided that it possesses a sufficient degree of hydrogen bonding to include the non-aqueous liquid.

When the matrix comprises a starch, it can be derived from native starch such as that derived from potato, maize or other plant sources. It is also possible to employ a chemically modified starch provided that it possesses a sufficient degree of hydrogen bonding to include the non-aqueous liquid.

When the matrix comprises keratin, it can be derived from animal wool, such as sheeps wool or from human hair.

When the matrix comprises casein, it can be derived from milk.

The most preferred polymer of which the matrix is comprised is cellulose, either native or regenerated.

The polysaccharide and/or protein which comprises the matrix can be provided as yarn or thread or as a woven sheet, or they can be in the form of a non-woven sheet or sponge-like material or as a powder, such as one having an average particle size of from $10\mu$ to 1 mm.

The non-aqueous liquid which is included in the matrix of the invention is one which has a dielectric constant, when normally measured at a temperature of from 0° to 25° C., of from 1.5 to 40. Preferably, the non-aqueous liquid has a dielectric constant of less than 40, most preferably from 2 to 30 and ideally from 2 to 10. Such ideal non-aqueous liquids having a dielectric constant of not more than 10 are essentially non-polar in character, the lower the dielectric constant, the more non-polar they are.

It is to be understood that the "non-aqueous liquid" which is included within the matrix can comprise a mixture of non-aqueous liquids which are mutually miscible. Where a mixture of liquids is included in the matrix, this mixture will have a dielectric constant, when normally measured at a temperature of from 0° to 25° C., of from 1.5 to 40.

Examples of non-aqueous liquids, together with their respective dielectric constants, are given in the following table:

| Non-aqueous Liquid | Approximate Dielectric Constant at 0° to 25° C. |
|---|---|
| Glycol | 38 |
| Nitrobenzene | 35 |
| Methanol | 33 |
| Ethanol | 24 |
| Benzoyl chloride | 23 |
| Lactic acid | 22 |
| Acetaldehyde | 21 |
| Acetone | 21 |
| n-propanol | 20 |
| propionaldehyde | 19 |
| iso-propanol | 18 |
| n-butanol | 17 |
| 1,2-dichloroethane | 10 |
| Ethyl lactate | 8 |
| Ethyl acetate | 6 |
| Acetic acid | 6 |
| Chlorobenzene | 6 |
| Methyl ether | 5 |
| Chloroform | 5 |
| Ethyl ether | 4 |
| Trichloroethylene | 4 |
| Propyl ether | 3 |
| Toluene | 2 |
| Xylene | 2 |
| Benzene | 2 |
| n-octane | 2 |
| Carbon tetrachloride | 2 |
| n-heptane | 2 |
| Cyclohexane | 2 |
| n-hexane | 2 |
| n-pentane | 2 |
| Turpentine | ~2 |
| White Spirit | ~2 |
| Light oil | ~2 |

It will be appreciated that the foregoing list of non-aqueous liquids is not exhaustive and that there are others having the requisite dielectric constant which could be included in the matrix of the article.

The choice of non-aqueous liquid will in general depend on the particular utility of the article; examples of uses of the article together with suitable non-aqueous liquids will be given later in this specification.

The non-aqueous liquid can also comprise a solution of an organic solvent, such as are examplified on the foregoing list, and a solute.

When the non-aqueous liquid is a solution, the solute which is dissolved in the organic solvent can be any substance which has a particular utility at the point of use when the included solution is released on contacting the article with water.

The solute can be liquid or solid at room temperature, provided that it is soluble in the organic solvent.

Examples of solutes are:

germicides, such as
   2,2'-methylene bis (3,4,6-trichlorophenol),
   2,4,4'-trichlorocarbanilide,
   3,4,4'-trichlorocarbanilide,
   2,5,4'-tribromosalicylanilide,
   3-trifluoromethyl-4,4'-dichlorocarbanilide,
   and 2,4,4'-trichloro-2'-hydroxydiphenyl
   - ether;

other antimicrobials, such as propyleneglycol, cetyl pyridinium chloride, alkyl dimethyl benzyl ammonium chloride, alkyl p-hydroxybenzoate, sorbic acid, cetyl dimethyl ether ammonium bromide (BRETOL), cetyl trimethyl ammonium bromide (BROMAT), cetyl trimethyl ammonium p-toluene sulphonate (CETATS), cetyl dimethyl benzyl ammonium chloride (CETOL), dichlorophene (G-4), hexachlorophene (G-11), diisobutyl phenoxy ethoxy ethyl dimethylbenzyl ammonium chloride (HYAMINE 1633), sodium dimethyl dithiocarbamate plus sodium 2-mercaptobenzothiazole (VANCIDE 51);

antifogs, such as dioctylester of sodium sulphosuccinic acid (AEROSOL OT-75%), organo silicone copolymer (UNION CARBIDE ORGANO MODIFIED FLUID L-77);

antiperspirants, such as aluminium chlorhydrate-propylene glycol complex (REHYDROL):

antistats, such as PEG-15 tallow polyamine (POLYQUART H), mink-amido-propyl dimethyl ammonium chloride (CERAPHYL 65);

fungicides, such as bisdimethylthiocarbamyl disulphide, N-trichloromethylthiotetrahydrophthalimide;

insect repellants, such as dimethylphthalate, 2-ethyl,1-3-hexanediol;

anti-inflammatory agents, such as indomethacin, salicylic acid, acetyl salicylic acid, and menthyl pyrrolidone carboxylate;

UV absorbers, such as menthyl salicylate, isobutyl p-aminobenzoate;

insecticides, such as pyrethrum, DDT, chlordane;

flavours and flavour modifiers, such as menthol, peppermint, clove, wintergreen, orange eucalyptus, aniseed, spearmint, rose, blackcurrant, bread, coffee, tea;

perfumes for providing any desirable fragrance; and deodorant perfumes, having the ability to reduce the development of personal body malodour or to deodorise kitchen or bathroom surfaces or enclosed spaces such as rooms. Examples of deodorant perfumes are given in U.S. Pat. No 4,288,341.

The quantity of solute to be employed in solution in the organic solvent will depend upon the solubility of the solute in the solvent and on the intended use of the article.

The weight of liquid included in the matrix of the article will generally not exceed an amount equal to the weight of the matrix. The actual amount of included liquid will also depend on the intended utility of the article, but this will generally form from 0.1% to 50% of the weight of the article. Usually, the amount of included liquid will form from 1 to 40%, preferably from 5 to 30%, most preferably from 10 to 25%, and ideally from 10 to 20% of the weight of the article.

Having regard to the fact that the article can comprise materials in addition to the matrix of polysaccharide and/or protein and included liquid, the amount of liquid included in the matrix can be expressed in terms of the relevant weight ratios. Thus, the weight ratio of the non-aqueous liquid to the matrix will normally be from 1:1000 to 1:1, preferably from 1:1000 to 1:2, most preferably from 1:1000 to 1:3 and ideally from 1:1000 to 1:4.

The article can be composed essentially of the matrix of polysaccharide and/or protein containing the included non-aqueous liquid, in which case the article will comprise from approximately 50 to 99% by weight of these polymers, the balance being the non-aqueous liquid. It is also possible for the article to comprise additionally other non-polysaccharide or non-protein materials such as synthetic polymers, for example, polyesters, polyamides and polyurethanes. Where a blend is employed, the matrix should comprise at least 10% and preferably at least 50% by weight of the article, as it is believed that polymers other than polysaccharide or protein possess little or no ability to include non-aqueous liquids compared with polysaccharide and proteins.

It is a property of the article of the invention that while maintained in a substantially dry-to-the-touch state, the non-aqueous liquid remains firmly included in the matrix to such an extent that any characteristic odour that it may normally possess is hardly detectable. When, however, the article is contacted with water, for example at the point of use, the non-aqueous liquid is almost instantaneously released from inclusion within the matrix and is available for delivery to an appropriate surface or enclosed space as desired.

Articles of the invention can, for example, take the form of yarn, thread or a woven or non-woven fibrous sheet, block or sponge-like material, or wools such as cotton wool and animal wool, or tablets or a powder.

Specific examples of articles of the invention are cellulose or woollen fabric articles for hospital, dental, domestic or cosmetic use such as absorbent applique, air fresheners, animal litter, bandages, bedpans, coffee, tea herb or spice bags, covers, bedspreads, bibs, brassieres, coveralls, cushioning and curtain fabrics, decontammination clothing, diapers, diaper liners, drapes, facial tissues, furniture padding, garment bags, gauze, handkerchiefs, head rests, interlining for coats, dresses, shirts and suits, mattress covers, medical wipes, napkins, operating room covers, packaging materials, pads, petticoats, pillow slips, stuffing and ticking, protective clothing, quilting, sanitary napkin covers and pads, sanitary towels, sheets, shirts, innersoles, liners, shoulder pads, shrouds, skirts, sleeping bags, socks, sponges, surface protectors, surgical dressing, tampons, tissues, towelling, tray liners, undergarments such as pants and vests, wash cloths, wiping cloths, wrapping materials and surgical plaster casts.

Articles of the invention can also take the form of a powder which can comprise an ingredient of a composition, especially a powdered composition, whose utility when contacted with water, and whose benefit is improved by release of non-aqueous liquid from the powder product ingredient at the time of use.

Such a composition can be composed essentially of the powder matrix containing the included non-aqueous liquid, in which case the composition will comprise from approximately 50 to almost 100% by weight of the powder article. It is more usual, however, for the composition to consist of a mixture of the powder article and other powder ingredients, for example, an abrasive such as calcite or a water-absorbent powder such as talc or a polymer having the ability to absorb an amount of water at least equal to its own weight. Where a blend of powders is employed, the powder article should comprise at least 1% and preferably at least 10% by weight of the product.

Specific examples of compositions comprising the powder article of the invention are powdered abrasive cleaning products for use for example in the bathroom or kitchen, powdered antiperspirant or deodorant products or face powders for topical application to human skin, powdered fruit drinks and powdered soup mixes.

It is to be understood that the above-mentioned examples of articles of the invention do not comprise an exhaustive list.

The articles of the invention are packaged in such a manner that they are contained within a closed container which is impervious to the ingress of moisture. Articles which are not so packaged can maintain their ability to retain included non-aqueous liquid for many months or even years, provided that the environment in which they are stored remains dry. However, under practical conditions of storage in the home, office, shop or factory, changing climatic conditions can bring about gradual release of the included non-aqueous liquid due to the presence of water vapour in the air.

It is to be understood that the gradual release of included non-aqueous liquid by water vapour can be of advantage, for example in the dispensing of deodorants, perfumes or insecticides in an enclosed space over a long period of time, but it is necessary in order to obtain maximum advantage of such a utility to store the articles prior to use in a moisture impervious package.

The packaging material and the shape and form of the package in which the articles of the invention are contained are not critical, provided that the package forms a closed, moisture impervious container.

The packaging material can for example be of a flexible nature, such as of flexible plastics material or metal foil or laminates of these materials, or it can for example be rigid in nature, such as of rigid plastics material or metal or glass. The packaging material can also be a liquid material which is sprayed or dip-coated onto the article to provide after drying a continuous moisture impervious film.

The package itself can take any of a variety of forms which suit the manufacturer or consumer. Examples are a sealed pouch or packet adapted to be torn open when required for use, or a reclosable lidded jar or canister which can contain a supply of the articles of the invention.

The invention also relates to a process for the manufacture of a substantially dry-to-the-touch article contained in a closed, moisture impervious container, which process comprises the steps of:
  (i) contacting a matrix of polysaccharide or protein or a mixture thereof with an aqueous liquid;
  (ii) subsequently contacting the matrix with a first non-aqueous liquid which is miscible with the aqueous liquid and which has a dielectric constant of from 1.5 to 40;
  (iii) drying the matrix to remove superficial remains of liquid to provide a dry-to-the-touch article; and
  (iv) packaging the article in a closed moisture impervious container.

The invention also relates to a process for the manufacture of a substantially dry-to-the-touch article contained in a closed, moisture impervious container, which process comprises the steps of:
  (i) contacting a matrix of polysaccharide or protein or a mixture thereof with a first non-aqueous liquid chosen from a $C_1$ to $C_4$ alkanol, aldehyde or ketone or mixtures thereof with water;
  (ii) subsequently contacting the matrix with a second non-aqueous liquid which is miscible with the first and which has a dielectric constant which is lower than that of the first non-aqueous liquid;
  (iii) drying the matrix to remove superficial remains of liquid to provide a dry-to-the-touch article; and
  (iv) packaging the article in a closed moisture impervious container.

Ideally, the matrix of polysaccharide and/or protein, following contact with the first non-aqueous liquid, is contacted successively with two or more further non-aqueous liquids, each being miscible with, and each having a dielectric constant at 0° to 25° C. of less than that of, the previous non-aqueous liquid. Irrespective of the number of successive non-aqueous liquids with which the matrix is contacted, the article, after drying to remove superficial traces of non-aqueous liquid to provide a substantially dry-to-the-touch article, will contain non-aqueous liquid included in it in such a manner that it is releasable when the article is contacted with water.

Examples of aqueous liquids are water or solutions of acids, bases or salts or $C_1$ to $C_4$ alkanols, aldehydes or ketones in water. Particularly preferred aqueous solutions are those containing sulphuric acid, sodium hydroxide or other electrolytes.

Examples of non-aqueous liquids, together with their respective dielectric constants at 0° to 25° C., or solutions that can comprise solvents and solutes, that can be employed in the process of the invention are given earlier in this specification.

It is an important aspect of the invention that consecutive liquids with which the matrix is contacted are miscible with each other. It is to be understood, however, that liquids which are normally immiscible with each other can be rendered miscible by employing a solubilising agent.

When transferring the matrix from contact with one liquid to the next of lower dielectric constant, it is essential not to dry the matrix; it is however preferable to drain excess liquid from the matrix before contacting it with the next successive liquid.

The temperature of each liquid with which the matrix is contacted or immersed will generally influence the rate of transfer of the liquid to the matrix. Usually, the higher the temperature of contact, the more rapidly the liquid is transferred to the matrix. The maximum temperature of contact will normally not exceed the boiling point, at normal atmospheric pressure, of the relevant non-aqueous liquid.

The duration of contact of the matrix with each liquid will generally also affect the amount of liquid transferred to the matrix. Generally, the time of contact should be from 1 minute to 30 minutes, it being apparent that a shorter contact time than 1 minute can result in inadequate uptake of liquid, whereas a longer contact time than 30 minutes is unlikely to result in any significant increase in the amount of liquid taken up by the matrix of polymeric fibres.

The process of the invention can be conducted in such a manner that pieces of matrix having the shape and size of the finished article are successively transferred from one liquid to another, preferably with a brief draining step between liquids so that carry over of one liquid to another with consequent adulteration or dilution of subsequent liquids is minimised. Alternatively, the matrix in the form of a continuous sheet, strip, filament or web can be fed successively through each liquid, emerging between liquids to allow excess superficial liquid to drain away or to be pressed away, for example by passage through a pair of rollers. In such a "continuous" process, the sheet, strip or web of matrix emerging from the "final" liquid can then be dried before packaging, for example as a roll, or before being cut into pieces of a suitable size for individual use.

The process of the invention and the articles thereby obtained are illustrated by the following examples.

EXAMPLE 1

This example illustrates the inclusion of n-heptane as the non-aqueous liquid in viscose rayon fabric (cellulose) as the polysaccharide matrix, to provide articles which are subsequently packaged.

Pieces of viscose rayon woven fabric measuring 5 cm×5 cm were first immersed in distilled water for 15 minutes and then transferred, after draining briefly, to a bath containing ethanol in which they were immersed for a further 15 minutes. The pieces of rayon fabric were then removed from the ethanol, drained briefly and then transferred, using the same procedure of dip and drain, in sequence to a series of baths each containing a different non-aqueous liquid. The sequence of liquids employed was therefore as follows:

water
ethanol
acetone
iso-propanol
chloroform
trichloroethylene
toluene
n-heptane After removal from the final bath containing n-heptane, the pieces of viscose rayon fabric were drained, and then vacuum dried in an oven at 85° C. for 4 hours.

The quantity of included non-aqueous liquid in the viscose rayon fabric articles was measured gravimetrically and by analysis of the proton $T_2$ nmr decay signal. The results confirmed that the dried viscose rayon article contained about 10% by weight of non-aqueous liquid.

The viscose rayon fabric article was odourless while in a dry state, but when sprayed with water, n-heptane was immediately released as evidenced from the odour of this hydrocarbon and from the fact that the article could be used to wipe clean an oily surface.

Articles of a similar nature were packaged in saran coated metathene bags and sealed to exclude moisture, while some similar articles were left unpackaged. The packaged articles retained their ability to release n-heptane on moistening with water, even after a period of storage at 20° C. for six months: the unpackaged articles slowly lost n-heptane after storage for only a few weeks, due to contact with water vapour in the air.

EXAMPLE 2

This example illustrates the degree to which n-heptane, as the non-aqueous liquid, can be included in heavyweight viscose rayon fabric, as the cellulose matrix, using twelve different sequences of organic liquids.

In each case 5 cm squares of viscose rayon fabric were immersed in each liquid according to the scheme shown in Table 1. The soaking time in each liquid was 15 minutes and the final drying time in each case was 5 hours at 85° C. in a vacuum oven.

The articles so produced can be subsequently packaged in moisture impervious containers.

TABLE 1
EFFECT OF LIQUID SEQUENCE ON INCLUSION

| LIQUID | DIELECTRIC CONSTANT | 2A | 2B | 2C | 2D | 2E | 2F | 2G | 2H | 2I | 2J | 2K | 2L |
|---|---|---|---|---|---|---|---|---|---|---|---|---|---|
| Water | 78 | ✓ | ✓ | ✓ | ✓ | ✓ | ✓ | ✓ | ✓ | ✓ | ✓ | ✓ | X |
| Ethanol | 24 | ✓ | ✓ | ✓ | ✓ | ✓ | ✓ | ✓ | X | X | X | X | ✓ |
| Acetone | 20 | ✓ | ✓ | ✓ | X | ✓ | X | X | X |  | ✓ | X | ✓ |
| iso-propanol | 18 | ✓ | ✓ | X | X | X | X | ✓ |  | X | X | ✓ | ✓ |
| Trichlorethylene | 3.5 | ✓ | X | X | X | ✓ |  | ✓ | ✓ | ✓ | X | X | ✓ |
| Heptane | 2 | ✓ | ✓ | ✓ | ✓ | ✓ | ✓ | ✓ |  |  |  |  | ✓ |
| % w/w inclusion of solvent* | | 12 | 5 | 1 | 1 | 1 | <1 | 7 | 5 | 1 | <1 | 2 | 4 |

*determined gravimetrically
X liquid omitted from sequence

It can be seen from this table that it was necessary for the heavyweight viscose rayon article to pass through each of the 5 non-aqueous liquids, after immersion in water, in order to achieve a maximum inclusion of 12% by weight of solvent which was mainly n-heptane. Omission of both acetone and iso-propanol (example 2F) resulted in very low inclusion of n-heptane, probably because trichlorethylene is immiscible with ethanol. This illustrates the importance of ensuring that consecutive non-aqueous liquids are miscible with each other.

Also, as can be seen from Example 2L, it is possible to initiate the inclusion process with a short chain alcohol such as ethanol, rather than with water.

In each of Examples 2A to 2L the included article should be packaged in a closed container which is impervious to moisture.

EXAMPLE 3

This example illustrates the inclusion of trichloroethylene as the non-aqueous liquid in mercerised cotton (cellulose matrix) to provide articles which were subsequently packaged.

Pieces of woven mercerised cotton fabric measuring 5 cm×5 cm were first immersed in distilled water for 15 minutes and then transferred, after draining briefly, to a bath containing ethanol in which they were immersed for a further 15 minutes. The pieces of cotton fabric were then removed from the ethanol, drained briefly and transferred, using the same procedure of dip and drain, in sequence to a series of baths each containing a different non-aqueous liquid. The sequence of liquids employed was therefore as follows:
water
ethanol
acetone
iso-propanol
chloroform
trichloroethylene After removal from the final bath containing trichloroethylene, the pieces of cotton fabric were drained, and then vacuum dried in an oven at 85° C. for 4 hours. The quantity of included non-aqueous liquid in the cotton fabric articles was measured gravimetrically and by analysis of the proton $T_2$ nmr decay signal.

The result of gravimetric and nmr measurements showed that the dried cotton article contained about 10% by weight of included non-aqueous liquid.

The cotton fabric article was odourless while in a dry state, but when sprayed with water, trichloroethylene was immediately released as evidenced from the odour of this chlorinated hydrocarbon and from the fact that the article could be used to wipe clean an oily surface.

Articles of a similar nature were packaged in saran coated metathene bags and sealed to exclude moisture, while some similar articles were left unpackaged. The packaged articles retained their ability to release trichloroethylene on moistening with water, even after a period of storage at 20° C. for 6 months: the unpackaged articles slowly lost trichloroethylene after storing for only a few weeks, due to contact with water vapour in the air.

EXAMPLE 4

This example illustrates the inclusion of ethyl lactate as the non-aqueous liquid in viscose rayon fabric (cellulose matrix), to provide articles which after bonding to adhesive plaster were individually packaged.

Pieces of viscose rayon woven fabric were first immersed in distilled water for 15 minutes and then transferred, after draining briefly, to a bath containing ethanol in which they were immersed for a further 15 minutes. The pieces of rayon fabric were then removed from the ethanol, drained briefly and then transferred, using the same procedure of dip and drain, in sequence to a series of baths each containing a different non-aqueous liquid, the final liquid being ethyl lactate. The sequence of liquids employed was therefore as follows:
water
ethanol
acetone
iso-propanol
ethyl lactate After removal from the final bath containing the ethyl lactate, the pieces of viscose rayon fabric were drained, and then vacuum dried in an oven at 85° C. for 4 hours. The quantity of included ethyl lactate, together with traces of the other non-aqueous liquids in the viscose rayon fabric article, was measured gravimetrically and it was shown that the dried viscose rayon article contained 12 to 16% by weight of organic liquid. This was mainly ethyl lactate.

The viscose rayon fabric article was odourless while in a dry state, but when sprayed with water, the ethyl lactate was immediately released as evidenced by the odour of ethyl lactate and the lowering of the pH of both the applied water and of the skin after application of the wetted fabric article.

The viscose rayon fabric article can be bonded to an adhesive dressing so as to give an occlusive plaster that, when in contact with moisture from the skin, will liberate gradually the included ethyl lactate and provide topical treatment for acne and other skin disorders.

Articles of a similar nature were packaged in saran coated metathene bags and sealed to exclude water and water vapour, while some similar articles were left unpackaged. The packaged articles retained their ability to release ethyl lactate on moistening with water, even after a period of storage at 20° C. for six months: the unpackaged articles slowly lost ethyl lactate after storage for only a few weeks, due to contact with water vapour in the air.

EXAMPLE 5

This example illustrates the inclusion of a solution of trichlorophenol (TCP) in iso-propanol as the non-aqueous liquid in viscose rayon fabric (cellulose matrix), to provide articles which are subsequently packaged.

Pieces of viscose rayon woven fabric measuring 5 cm×5 cm were first immersed in distilled water for 15 minutes and then transferred, after draining briefly, to a bath containing ethanol in which they were immersed for a further 15 minutes. The pieces of rayon fabric were then removed from the ethanol, drained briefly and then transferred, using the same procedure of dip and drain, in sequence to a series of baths each containing a different non-aqueous liquid, the final liquid being a 10% by weight solution of TCP in iso-propanol. The sequence of liquids employed was therefore as follows:
water
ethanol
acetone
10% by weight TCP in iso-propanol After removal from the final bath containing the TCP solution, the pieces of viscose rayon fabric were drained, and then vacuum dried in an oven at 85° C. for 4 hours.

The quantity of included solution, together with traces of residual ethanol and acetone in the viscose rayon fabric articles was measured gravimetrically. The results confirmed that the dried viscose rayon article contained about 8 to 9% by weight of non-aqueous liquid which was mainly the solution of TCP in iso-propanol.

The articles so produced were subsequently packaged individually in moisture impervious metal foil pouches.

The viscose rayon fabric article was odourless while in a dry state, but when sprayed with water, the solution of TCP in iso-propanol was immediately released as evidenced from the odour of TCP and from the fact that the article could be used to sanitise human skin.

EXAMPLE 6

This example illustrates the inclusion of a solution of the germicide, 2,4,4'-trichloro-2'-hydroxydiphenylether (DP 300) in iso-propanol as the non-aqueous liquid in viscose rayon fabric (cellulose matrix), to provide germicidal wipe articles which were subsequently packaged.

Pieces of viscose rayon woven fabric were first immersed in distilled water for 15 minutes and then transferred, after draining briefly, to a bath containing ethanol in which they were immersed for a further 15 minutes. The pieces of rayon fabric were then removed from the ethanol, drained briefly and then transferred using the same procedure of dip and drain, in sequence to a series of baths each containing a different non-aqueous liquid, the final liquid being a 0.2% by weight solution of DP 300 germicide in iso-propanol. The sequence of liquids employed was therefore as follows:
water
ethanol
acetone
iso-propanol
0.2% DP 300 in iso-propanol After removal from the final bath containing the DP 300 solution, the pieces of viscose rayon fabric were drained, and then vacuum dried at 85° C. for 4 hours.

The quantity of included solution, together with traces of the other organic liquids, in the viscose rayon fabric was measured gravimetrically and it was shown that the viscose rayon article contained about 8% of DP 300 solution in iso-propanol.

The viscose rayon fabric article was odourless while in a dry state, but when sprayed with water, the DP 300 solution was immediately released as evidenced by the odour of iso-propanol and the ability of the wetted article to inhibit completely microbial growth on a glass slide after wiping with the wetted article.

Articles of a similar nature were packaged in saran coated metathene bags and sealed to exclude water and water vapour, while some similar articles were left unpackaged. The packaged articles retained their ability to release DP 300 solution on moistening with water, even after a period of storage at 20° C. for six months: the unpackaged articles slowly lost DP 300 solution after storage for only a few weeks, due to contact with water vapour in the air.

EXAMPLE 7

This example illustrates the inclusion of a solution of a perfume in n-heptane, as the non-aqueous liquid, in a cellulose powder of particle size 15–40 microns (cellulose matrix), to provide a powder article for incorporation into a hard surface scouring powder or a deodorant powder which are subsequently packaged.

The cellulose powder was placed in a glass column and distilled water added such that the cellulose powder was completely wetted. After an immersion time of 5 minutes the excess water was drained from the column and ethanol added onto the top of the cellulose powder in the column. The ethanol was allowed to percolate through the cellulose powder for 5 minutes and then drained and replaced similarly with each of the series of different non-aqueous liquids, the final liquid being a 10% volume solution of a perfume in n-heptane. The sequence of liquids employed were therefore as follows:
water
ethanol
acetone
iso-propanol
trichloroethylene
10% volume solution of perfume in n-heptane After the final solution had drained from the column the cellulose powder was removed and vacuum dried in an oven at 85° C. for 4 hours.

The quantity of included solution in the cellulose powder matrix so obtained was measured gravimetrically and was shown to form about 8% by weight.

The cellulose powder article so produced was odourless when in a dry state, but when sprayed with water the solution of perfume in n-heptane was immediately released as evidenced by the characteristic smell of the particular perfume in solution.

The cellulose powder product may be incorporated, for example, into
(i) a calcite base, to give a final perfume level of 0.1–0.2% for use as a hard surface scouring powder; and
(ii) a talc base, to give a final perfume level as required for use as a deodorant talcum powder or antiperspirant.

The above powdered compositions are packaged in dispensing cannisters and sealed to exclude moisture.

EXAMPLE 8

This example illustrates the inclusion of a solution of Florida orange flavour in iso-propanol as the non-aqueous liquid in viscose rayon fabric (cellulose matrix), to provide an article which is subsequently packaged.

Pieces of viscose rayon woven fabric measuring 5 cm×5 cm were first immersed in distilled water for 15 minutes and then transferred, after draining briefly, to a bath containing ethanol in which they were immersed for a further 15 minutes. The pieces of rayon fabric were then removed from the ethanol, drained briefly and then transferred, using the same procedure of dip and drain, in sequence to a series of baths each containing a different non-aqueous liquid, the final liquid being a 5% by weight solution of orange flavour in iso-propanol. The sequence of liquids employed was therefore as follows:
 water
 ethanol
 acetone
 5% by weight solution of orange flavour in iso-propanol After removal from the final bath of liquid, the pieces of viscose rayon fabric were drained, and then vacuum dried in an oven at 85° C. for 4 hours.

The quantity of included non-aqueous liquid in the viscose rayon fabric articles was measured gravimetrically. The results confirmed that the dried viscose rayon article contained about 8% by weight of non-aqueous liquid.

The articles so produced were packaged in moisture impervious containers.

The viscose rayon fabric article was odourless while in a dry state, but when sprayed with water, the solution of orange flavour in iso-propanol was immediately released as evidenced from the smell of orange and the taste of orange when placing the dry fabric article in the mouth.

EXAMPLE 9

The procedure of Example 8 was repeated using separately spearmint flavour, rose flavour and aniseed in place of the Florida orange flavour.

Similar results were obtained.

EXAMPLE 10

This example illustrates the inclusion of a solution of 33 parts L-menthol to 67 parts Brazilian peppermint oil in n-heptane as the non-aqueous liquid in viscose rayon yarn (Tenasco Super) (cellulose matrix), to provide articles which are subsequently packaged.

Lengths of viscose rayon yarn were first immersed in distilled water for 15 minutes and then transferred, after draining briefly, to a bath containing ethanol in which they were immersed for a further 15 minutes. The lengths of yarn were then removed from the ethanol, drained briefly and then transferred, using the same procedure of dip and drain, in sequence to a series of baths each containing a different non-aqueous liquid. The sequence of liquids employed was therefore as follows:
 water
 ethanol
 acetone
 iso-propanol
 trichloroethylene
 10% by weight solution of 33:67 L-menthol: Brazilian peppermint oil in n-heptane After removal from the final bath containing the n-heptane solution, the lengths of viscose rayon yarn were drained, and then vacuum dried in an oven at 85° C. for 4 hours.

The quantity of included non-aqueous liquid in the viscose rayon fabric articles was measured gravimetrically. The results confirmed that the dried viscose rayon article contained about 10% by weight of the L-menthol Brazilian peppermint oil solution in n-heptane.

The viscose rayon yarn was odourless while in a dry state, but when sprayed with water, the solution in n-heptane of L-menthol Brazilian peppermint was immediately released as evidenced from the odour of peppermint and from the taste of both peppermint and menthol when placing the yarn in the mouth.

The viscose rayon yarn so produced is suitable for use as dental floss and can be packaged in moisture impermeable pouches of plastics material until required for use.

EXAMPLE 11

This example illustrates the inclusion of trichloroethylene as the non-aqueous liquid in woven wool fabric (keratin matrix), to provide articles which are subsequently packaged.

Pieces of wool fabric measuring 5 cm×5 cm were first immersed in distilled water for 15 minutes and then transferred, after draining briefly, to a bath containing ethanol in which they were immersed for a further 15 minutes. The pieces of wool fabric were then removed from the ethanol, drained briefly and then transferred, using the same procedure of dip and drain, in sequence to a series of baths each containing a different non-aqueous liquid, the final liquid being trichloroethylene. The sequence of liquids employed was therefore as follows:
 water
 ethanol
 acetone
 iso-propanol
 trichloroethylene After removal from the final bath containing trichloroethylene, the pieces of wool fabric were drained, and then vacuum dried in an oven at 85° C. for 4 hours.

The quantity of included non-aqueous liquid in the wool fabric articles was measured gravimetrically. The results confirmed that the dried woollen article contained about 10% by weight of non-aqueous liquid.

The woollen articles were subsequently packaged in a moisture impervious container.

The woollen article was odourless while in a dry state, but when sprayed with water, trichloroethylene was immediately released as evidenced from its odour.

EXAMPLE 12

This example illustrates the inclusion of trichloroethylene as the non-aqueous liquid in a non-woven cellulose fabric (J-cloth) (cellulose matrix), to provide wipe articles which are packaged in an airtight screw-topped jar.

Pieces of non-woven cellulose fabric measuring 5 cm×5 cm were first immersed in distilled water for 15 minutes and then transferred, after draining briefly, to a bath containing ethanol in which they were immersed for a further 15 minutes. The pieces of fabric were then removed from the ethanol, drained briefly and then transferred, using the same procedure of dip and drain, in sequence to a series of baths each containing a different non-aqueous liquid. The sequence of liquids employed was therefore as follows:

water
ethanol
acetone
iso-propanol
trichloroethylene

After removal from the final bath containing trichloroethylene, the pieces of non-woven cellulose fabric were drained, and then vacuum dried in an oven at 85° C. for 4 hours.

The quantity of included non-aqueous liquid in the non-woven cellulose fabric articles was measured gravimetrically. The results confirmed that the dried viscose rayon article contained about 6% by weight of non-aqueous liquid.

The J-cloth articles were packaged in a screw-topped moisture impervious jar.

The non-woven cellulose fabric article was odourless while in a dry state, but when sprayed with water, trichloroethylene was immediately released as evidenced from the odour of this solvent and from the fact that the article could be used to wipe clean an oily surface.

EXAMPLE 13

This example illustrates the inclusion of a deodorant perfume, as the non-aqueous liquid, in a wad of woven cellulose fabric (cellulose matrix) to provide a humidity controlled room deodorant (air freshener), which is packaged in a film of plastics material until required for use.

A wad of woven cellulose fabric measuring 10 cm long, 3 cm wide and 1 cm thick is first immersed in distilled water for 15 minutes and then transferred, after draining briefly, to a bath containing ethanol in which it is immersed for a further 15 minutes. The wad of cellulose fabric is then removed from the ethanol, drained briefly and then transferred, using the same procedure of dip and drain, in sequence to a series of baths each containing a different non-aqueous liquid. The sequence of liquids employed is as follows:

water
ethanol
iso-propanol
toluene
deodorant perfume No 1

The deodorant perfume, which is an example of a solution comprising a solvent and a solute, had the following formulation:

| Deodorant Perfume Formulation 1 | Parts by weight |
|---|---|
| Amber AB 358 | 3.0 |
| iso-Amyl salicylate | 5.0 |
| Benzyl salicylate | 4.0 |
| Bergamot AB 430 | 15.0 |
| o-t-Butylcyclohexyl acetate | 0.5 |
| Cedar atlas oil | 5.0 |
| Citronellol | 7.0 |
| Citronella oil | 16.1 |
| Citronellyloxyacetaldehyde | 0.5 |
| Geranium base 76 | 4.0 |
| 1,3,4,6,7,8-Hexahydro-4,6,6,7,8,8-hexamethyl-cyclopenta-γ-2-benzopyran | 10.0 |
| Hexyl aldone | 0.7 |
| Jasmin AB 284 | 12.0 |
| LRG 201 | 5.0 |
| Nonanolide-1:4 | 0.2 |

| Deodorant Perfume Formulation 1 | Parts by weight |
|---|---|
| Opoponax resinoid | 1.7 |
| Orange oil sweet | 8.0 |
| 10-Undecen-1-al | 0.30 |
| Vetyvert oil | 2.0 |
| | 100.00 |

After removal from the final bath containing the deodorant perfume, the wad of cellulose fabric is drained and then vacuum dried in an oven at 80° C. for 2 hours.

The quantity of included non-aqueous liquid in the wad of cellulose fabric will form from 4 to 10% by weight of the article. The wad of cellulose fabric can then be packaged in a vented carton shrink-wrapped with a film of plastics material.

When required for use as a room deodoriser, the shrink-wrapping can be removed and the deodorant perfume treated article enclosed in its vented carton can be placed in a room such as a kitchen or bathroom. While the atmosphere of the room is relatively dry, little or no deodorant perfume will be released from the article, but when the humidity increases, for example when the kitchen is used for cooking or the bathroom used for bathing, the water vapour in the air will trigger the release of at least a small portion of the deodorant perfume.

The article can accordingly be used for a period of weeks or months in order to freshen the air of the room in which it is placed.

EXAMPLE 14

The procedure of Example 13 can be repeated using a cellulose tissue/cottonwool article such as diapers, diaper liners and sanitary towels (cellulose matrix) in place of the woven cellulose fabric wad of that example.

The liquids with which the diapers, diaper liners or sanitary towels are treated can be varied according to the following sequence:

water
acetone
iso-propanol
trichloroethylene
deodorant perfume No 2, 10% solution in n-heptane, having the following formulation:

| Deodorant Perfume Formulation 2 | Parts by weight |
|---|---|
| 6-Acetyl-1,1,3,4,4,6-hexamethyl-tetrahydro naphathanlene | 3.00 |
| Bergamot base 37 | 20.00 |
| Carvacrol | 3.50 |
| Citronellyl acetate | 5.00 |
| Dipropylene glycol | 4.75 |
| Geranyl nitrile | 1.50 |
| Indole | 1.00 |
| Lemongrass oil | 3.00 |
| Lime AB 402 | 10.00 |
| Lavandin oil | 4.00 |
| 1-Menthol | 8.00 |
| 3a-Methyl-dodecahydro-6,6,9a-trimethyl-naphtho-2(2,1-b)-furan | 0.25 |
| β-Methyl naphthyl ketone | 5.00 |
| β-Naphthol methyl ether | 9.00 |
| Neroli base 78 | 6.00 |
| Pomeransol AB 314 | 6.00 |
| Petitgrain oil (terpeneless) | 4.00 |
| Orange oil sweet | 5.00 |
| Thyme oil red | 1.00 |

| Deodorant Perfume Formulation 2 | Parts by weight |
|---|---|
| | 100.00 |

EXAMPLE 15

The procedure of Example 13 can be repeated using cotton gauze article (cellulose matrix) for use as innersoles for shoes.

The liquids with which the cotton gauze article is treated can be varied according to the following sequence:
- water
- ethanol
- acetone
- iso-propanol
- deodorant perfume No 3, (10% in n-heptane), having the
- following formulation:

| Deodorant Perfume Formulation 3 | Parts by weight |
|---|---|
| p-t-Amylcyclohexanone | 5.00 |
| Benzoin Siam resinoid | 5.00 |
| Bergamot AB 430 | 15.00 |
| Coumarin | 4.00 |
| Diethyl phthalate | 4.35 |
| Geranium oil | 5.00 |
| Hercolyn D | 12.25 |
| 1,3,4,6,7,8-Hexahydro-4,6,6,7,8,8-hexamethylcyclopenta-$\gamma$-2-benzopyran | 3.00 |
| Lavandin oil | 10.00 |
| $\alpha$-iso-Methyl ionone | 12.00 |
| Mousse de chene yugo | 1.25 |
| Musk ambrette | 3.00 |
| Pimento leaf oil | 10.00 |
| Rosenta AB 380 | 10.00 |
| Rose-D-oxide | 0.15 |
| | 100.00 |

EXAMPLE 16

The procedure of Example 13 can be repeated using cellulose tissue paper for use as disposable wipes, bed linen or clothing (cellulose articles) in place of the woven cellulose fabric wad of that example.

The liquids with which the cellulose tissue paper is treated can be varied according to the following sequence:
- water
- methanol
- iso-propanol
- deodorant perfume No 4, (10% in n-heptane), having the
- following formulation:

| Deodorant Perfume Formulation 4 | Parts by weight |
|---|---|
| Bergamot AB 430 | 8.00 |
| p-t-Butylcyclohexyl acetate | 4.30 |
| Citronella oil | 6.00 |
| Diethyl phthalate | 8.25 |
| Ethyl vanillin | 0.20 |
| iso-Eugenol | 5.00 |
| Green Herbal AB 502 | 15.00 |
| 2-n-Heptylcyclopentanone | 0.50 |
| Indole | 1.50 |
| Inonyl formate | 5.00 |
| LRG 201 | 1.25 |
| $\alpha$-iso-Methyl ionone | 5.00 |
| $\beta$-Naphthol methylether | 7.50 |

| Deodorant Perfume Formulation 4 | Parts by weight |
|---|---|
| Nonanediol-1:3-diacetate | 4.00 |
| Patchouli oil | 7.00 |
| Phenylethyl phenyl acetate | 5.00 |
| Rosenta AB 380 | 6.00 |
| Sandalone | 4.00 |
| Tetrahydro muguol | 6.00 |
| $\gamma$-Undecalactone | 0.50 |
| | 100.00 |

EXAMPLE 17

The procedure of Example 13 can be repeated using a wood chip/saw dust material (cellulose matrix) to provide an animal litter article, such as cat litter, in place of the woven cellulose wad of that example.

The liquids with which the wood chip/saw dust is treated can be varied according to the following sequence:
- water
- ethanol
- iso-propanol
- deodorant perfume No 5, (5% in n-heptane), having the
- following formulation:

| Deodorant Perfume Formulation 5 | Parts by weight |
|---|---|
| 6-Acetyl-1,1,3,4,6-Hexamethyl tetrahydro naphthalate | 2.5 |
| p-t-Amylcyclohexanone | 0.06 |
| Benzyl salicylate | 15.0 |
| Bergamot AB 430 | 15.0 |
| Cinnamic alcohol | 5.0 |
| Diethyl phthalate | 8.04 |
| Dimethyl benzyl carbinyl acetate | 2.5 |
| Dimyrcetol | 16.0 |
| Dipropylene glycol | 14.25 |
| Geraniol | 5.0 |
| Isobutyl phenyl acetate | 5.0 |
| 3a-methyl-dodecahydro-6,6,9a-trimethyl-naphtho-2(2,1-b)furan | 0.75 |
| Methyl salicylate | 0.5 |
| Mousse de Chene Yougo | 6.0 |
| Nonanolide-1:4 | 0.2 |
| Pelargene | 4.0 |
| Trichloromethyl phenyl carbinyl acetate | 0.2 |

EXAMPLE 18

The procedure of Example 13 can be repeated using a woven cotton or linen fabric material (cellulose matrix) to provide material for making up curtains and loose covers for chairs and settees, in place of the woven cellulose wad of that example.

The liquids with which the woven cotton or linen fabric is treated can be varied according to the following sequence:
- water
- ethanol
- iso-propanol
- deodorant perfume No 6, (10% in n-heptane) having the
- following formulation:

| Deodorant Perfume Formulation 6 | Parts by weight |
|---|---|
| Benzyl propionate | 4.0 |
| Bergamot oil | 15.0 |
| o-t-Butylcyclohexyl acetate | 2.0 |

-continued

| Deodorant Perfume Formulation 6 | Parts by weight |
|---|---|
| p-t-Butyl-αButyl-α-methyl hydrocinnamic aldehyde | 15.0 |
| Clove leaf oil | 10.0 |
| Diethyl phthalate | 9.25 |
| Dimethyl benzyl carbinyl acetate | 5.0 |
| Ionyl acetate | 10.0 |
| Iso-butyl benzoate | 5.0 |
| LRG-201 | 1.25 |
| 3a-Methyl-dodecahydro-6,6,9a-trimethyl-naphtho-2(2,1-b)furan | 0.5 |
| Neroli oil | 3.0 |
| Petitgrain oil | 10.0 |
| Phenyl ethyl alcohol | 10.0 |

Curtain material and chair covers so treated can be lightly sprayed with water when necessary to release a small quantity of this deodorant perfume to dispel unpleasant odour, such as stale tobacco smoke, with which such material can become tainted.

EXAMPLE 19

This example illustrates the inclusion of a Florida orange flavour, as the non-aqueous liquid, in powdered casein (protein matrix) to form the basis of a dry powdered ('instant') beverage.

20 g of powdered water-insoluble casein were first stirred vigorously in water for 15 minutes and then the water was drained off on a sintered glass funnel. The water-moist powder was then resuspended in ethanol for a further 15 minutes before the ethanol was drained-off in a similar manner. This procedure was repeated firstly with acetone and finally with a 5% solution of Florida orange flavour concentrate (solute) in iso-propanol (solvent).

After finally draining off surplus orange flavour solution, the powdered casein was dried in a vacuum oven at 85° C. for 2 hours, after which time it was found to be odourless.

Moistening of the dry powder (article) with water released a very strong aroma of orange.

The casein powder containing included orange flavour dissolved in isopropanol can be used as an ingredient of an 'instant' fruit drink and should be packaged together with other ingredients in a moisture impervious container.

EXAMPLE 20

This example illustrates the inclusion of a blackcurrant flavour (dissolved in isopropanol), as the non-aqueous liquid, in powdered starch (polysaccharide matrix) to form the basis of a dry powdered ('instant') beverage.

50 g powdered maize starch are first stirred with 200 ml water for 15 minutes and then the water is drained off on a sintered glass funnel. The water-moist powder is then resuspended in 200 ml ethanol for a further 15 minutes with stirring before the ethanol is drained off in a similar manner. This procedure is repeated with a 200 ml portion of acetone and then with a similar volume of blackcurrant flavour (solute) as a 5% by weight solution in isopropanol (solvent).

The blackcurrant flavour (solute) can have the following formulation:

| Blackcurrent flavour | % w/w |
|---|---|
| p-Hydroxyphenylbutanone | 2.0 |
| Vanillin | 0.5 |

-continued

| Blackcurrent flavour | % w/w |
|---|---|
| Dimethyl sulphide | 0.5 |
| Acetaldehyde | 2.0 |
| Acetic acid | 4.0 |
| Ethyl acetate | 8.5 |
| Ethyl butyrate | 3.0 |
| Ethyl-3-methyl butyrate | 1.5 |
| cis-3-hexenyl formate | 0.2 |
| cis-3-hexenyl-2-methyl butanoate | 1.0 |
| Oil buchu | 0.2 |
| Blackcurrant bud absolute | 0.02 |
| Benzyl alcohol | 5.0 |
| 4-methyl-4-mercaptopentan-2-one | 0.0003 |
| Benzyl benzoate | 2 |
| 4-Hydroxy undecanoic acid lactone | 0.3 |
| 1,8 Epoxy-p-methane | 0.1 |
| iso-Propanol | to 100 |

After finally draining off surplus blackcurrant flavour solution, the powdered maize starch is dried in a vacuum oven at 85° C. for 2 hours after which time it is odourless.

Moistening of the dry powder (article) with water releases a very strong aroma and flavour of blackcurrant.

The dry powder article can be employed as the blackcurrant flavour ingredient in a dry powdered mix suitable for the preparation of a fruit drink on addition of water.

The dry powdered mix, which should be packed in a moisture impervious container until required for use, can have the following formulation:

|  | % w/w |
|---|---|
| Sugar | 96.0 |
| Citric acid | 1.75 |
| Gum | 0.67 |
| Tricalcium phosphate | 0.26 |
| Vitamin C | 0.4 |
| Sodium citrate | 0.53 |
| Blackcurrant flavour ingredient | 0.39 |
| Colour | q.v. |

20 g of the dry powdered mix can be stirred with 200 ml water to provide a refreshing blackcurrant fruit drink.

EXAMPLE 21

This Example illustrates the inclusion of a curry flavour, as the non-aqueous liquid, in powdered starch (polysaccharide matrix) to form an ingredient (article) for the preparation of a curry dish.

The procedure of Example 20 can be repeated except that the powdered starch used is cornflour (polysaccharide matrix) and the flavour used in the final treatment with a non-aqueous liquid is a 5% by weight solution of a curry flavour in iso-propanol.

The curry flavour can have the following formulation:

|  | % w/w |
|---|---|
| Oleoresin cumin | 38.46 |
| Oleoresin coriander | 30.77 |
| Oleoresin celery | 11.54 |
| Black pepper oil | 11.54 |
| Cumin oil | 7.69 |

The dry curry powder (article), although odourless in the dry state, can be used in the preparation of curry dishes when the flavour of curry is released on contact with water.

EXAMPLE 22

This example illustrates the inclusion of an earl grey tea flavour in a perforated non-woven cellulose bag (tea bag) for enhancing the flavour properties of low grade tea leaf enclosed in such a bag.

Perforated non-woven cellulose tissue material, suitable for the production of tea bags, in the form of a continuous web is passed through water and then a series of solvents, namely ethanol, acetone and finally iso-propanol containing 5% of an earl grey tea flavour, having the following formulation:

|  | % w/w |
|---|---|
| Bergamot oil | 95 |
| Rose oil | 3 |
| Lemon oil | 2 |

The residence time in each liquid is 15 minutes, and between each liquid the web is passed through the nip of a pair of rollers to squeeze out surplus liquid before passing to the next liquid. The web is not allowed to dry out during passage from one liquid to the next.

The web of material after passing through the final liquid, i.e. the solution of earl grey tea flavour, is thoroughly dried at 85° C. for 3 hours and then it is formed into pouches 4 cm square and partly filled with leaf tea and the pouches are finally closed to retain the leaf tea.

The pouches are finally packed in batches of 10 in moisture impervious foil containers.

The pouches (tea bags) can be used with infusion in hot water to provide an excellent cup of tea having a superior aroma and flavour of earl grey tea.

EXAMPLE 23

This example illustrates the inclusion of a bread flavour (non-aqueous liquid) in a paper wrapper (cellulose matrix) for wrapping freshly baked bread.

The procedure described in Example 22 can be repeated, except that the perforated non-woven cellulose tissue employed is in the form of a web 40 cm wide, i.e. of a dimension suitable for wrapping loaves of bread, and the flavour employed is a bread flavour at a concentration of 5% by weight in iso-propanol (non-aqueous liquid). The bread flavour can have the following formulation:

|  | % w/w |
|---|---|
| iso-Butanol | 1.274 |
| Glacial acetic acid | 1.274 |
| Butyric acid | 1.274 |
| iso-Butyric acid | 0.644 |
| Pentanoic acid | 0.32 |
| Hexanoic acid | 0.644 |
| β-Phenyl ethyl alcohol | 3.8 |
| α-Nonalactone | 0.644 |
| Phenyl acetic acid | 0.126 |
| iso-Propanol | 90.0 |

The dried web of non-woven cellulose tissue containing included in it the above bread flavour (the article) should be stored in a moisture impervious container until required for use, to avoid premature release of bread flavour due to atmospheric water vapour. The treated tissue article can then subsequently be employed to wrap loaves of freshly baked bread.

The water vapour released from fresh baked bread is sufficient to release slowly and in a controlled manner sufficient of the bread flavour to maintain the loaves of bread in an apparent fresh state even after long storage.

To ensure that bread flavour is not prematurely released from loaves of bread wrapped in the treated cellulose material, a moisture impervious outer wrapping of polyethylene film can be applied until the bread is required for display or consumption.

Bread flavour can also be released from the treated cellulose wrapping material by lightly spraying in with water. This can provide an aroma of freshly baked bread, even though the bread may have been baked many months earlier and stored in a frozen state to avoid microbial spoilage and staling.

EXAMPLE 24

This Example illustrates the inclusion of a herbal-spicy flavour (non-aqueous liquid) in a woven cotton material (cellulose matrix) used for making in bags to contain herbs and spices for use in the flavouring of stews or soups.

The procedure described in Example 23 can be repeated, except that the flavour employed is a 5% solution of a 'bouquet garni' flavour in iso-propanol. The 'bouquet garni' flavour can have the following formulation:

|  | % w/w |
|---|---|
| Oleoresin thyme | 12.0 |
| Oleoresin celery | 60.0 |
| Oleoresin mace | 10.0 |
| Oleoresin clove | 4.0 |
| Bay oil | 3.0 |
| Oreganum oil | 4.0 |
| Onion oil | 0.4 |
| Carrotseed oil | 6.6 |

The dry cellulose woven cotton material containing the included 'bouquet garni' flavour (article) can be used to make into bags and filled with dried herbs and spices as desired. The filled bags should be packaged in a moisture impervious container until required for use. When introduced into a stew or stock for soup, the 'bouquet garni' flavour will be released due to contact with water to provide added flavour to the dish to which it has been added.

EXAMPLE 25

This Example illustrates the inclusion of a perfume (non-aqueous liquid) into a linen and cotton roller towel (cellulose matrix) which is intended to be wrapped in a moisture impervious film of plastics material until required for use.

A web of soiled linen and cotton towelling 30 cm wide of the type employed in roller towel dispensers is first laundered according to conventional laundering techniques, but while still damp with residual water is passed on a continuous basis through a series of tanks containing organic solvents in the following sequence: ethanol, followed by acetone, followed by iso-propanol, followed by a 1% by weight solution of a rose perfume in n-heptane.

The perfume employed can have the following formulation:

| Rose Perfume Components | % w/w |
| --- | --- |
| Citronellol | 10.0 |
| Hydroxycitronellal | 10.0 |
| Phenyl ethyl alcohol | 23.0 |
| Tetrahydro geraniol | 07.0 |
| Methyl ionone | 08.0 |
| Phenyl ethyl acetate | 07.0 |
| Cyclamen aldehyde | 05.0 |
| Amyl cinnamic aldehyde | 07.0 |
| Linalol | 10.0 |
| Eugenol | 01.0 |
| Citronellyl formate | 05.0 |
| Anisic aldehyde | 03.0 |
| Rose oxide 10% | 02.0 |
| Phenyl acetic aldehyde dimethyl acetal | 02.0 |

The web of towelling is allowed to contact each liquid for 10 minutes and is passed through the nip of a pair of rollers between tanks to remove surplus liquid. The towelling is not permitted to dry out between treatments.

The web of towelling after passage through the final tank containing the perfume solution is dried, rolled and packaged in a film of plastics material.

When required for use, the roller towel is unpacked and placed on a roller dispenser. Contact with wet hands is sufficient to release a pleasant fragrance of rose perfume. The inner layers of treated towelling within the dispenser are suitably protected by the outer layer from atmospheric water vapour to ensure that perfume is not prematurely released due to the damp atmosphere of the washroom.

A roller towel so treated is suitable for use in a ladies washroom.

EXAMPLE 26

The procedure of Example 25 can be repeated using a pine needle green sweet perfume having the following formulation:

| Pine Needle Green Sweet Perfume Components | % w/w |
| --- | --- |
| Aldehyde $C_9$ 10% | 0.5 |
| Aldehyde $C_{10}$ 10% | 1.0 |
| Methyl nonyl aldehyde 10% | 3.0 |
| Anisic aldehyde | 5.0 |
| Bergamot synthetic | 8.0 |
| Bornyl acetate | 50.0 |
| Citronellol | 2.0 |
| Coumarin | 5.0 |
| Geranyl acetate | 3.0 |
| Lavandin | 2.0 |
| Lixetone | 2.5 |
| Musk ambrette | 2.0 |
| p-Tertiary butyl cyclohexyl acetate | 3.0 |
| Terpinoline | 5.0 |
| Versalide | 2.0 |
| Galbanum | 0.5 |
| Orange oil sweet | 0.8 |
| Rosemary | 2.0 |
| Linalyl acetate | 1.7 |
| Elemi gum | 1.0 |

A roller towel so treated is suitable for use in a mens' washroom.

What is claimed is:

1. A substantially dry-to-the-touch article contained in a closed, moisture impervious container, the article comprising:
    (i) a matrix of polymer selected from the group consisting of polysaccharide, protein and mixtures thereof; and
    (ii) a non-aqueous liquid, having a dielectric constant of from 1.5 to 40, included within the matrix;
the weight ratio of the non-aqueous liquid to the matrix being from 1:1000 to 1:1; the non-aqueous liquid being included in the matrix in such a manner that it is releasable when the article is contacted with water.

2. The article according to claim 1, wherein the polysaccharide is cellulose.

3. The article according to claim 2, wherein the cellulose is regenerated cellulose.

4. The article according to claim 2, wherein the cellulose is a chemically modified cellulose.

5. The article according to claim 1, wherein the polysaccharide is starch.

6. The article according to claim 5, wherein the starch is a chemically modified starch.

7. The article according to claim 1, wherein the protein is keratin.

8. The article according to claim 7, wherein the keratin is derived from hair selected from the group consisting of animal wool, human hair and mixtures thereof.

9. The article according to claim 1, wherein the protein is casein.

10. The article according to claim 1, wherein the non-aqueous liquid has a dielectric constant of from 2 to 30.

11. The article according to claim 1, wherein the non-aqueous liquid comprises an organic solvent containing dissolved therein a solute.

12. The article according to claim 1, wherein the weight ratio of the non-aqueous liquid to the matrix is from 1000 to 1:2.

13. A process for the manufacture of a substantially dry-to-the-touch article contained in a closed moisture impervious container, according to claim 1, which process comprises the steps of:
    (i) contacting the matrix of polysaccharide and/or protein with an aqueous liquid;
    (ii) subsequently contacting the matrix with a first non-aqueous liquid which is miscible with the aqueous liquid and which has a dielectric constant of from 1.5 to 40;
    (iii) drying the matrix to remove superficial remains of liquid to provide a dry-to-the-touch article; and
    (iv) packaging the article in a closed moisture impervious container.

14. A process for the manufacture of a substantially dry-to-the-touch article contained in a closed, moisture impervious container according to claim 1, which process comprises the steps of:
    (i) contacting the matrix of polysaccharide and/or protein with a first non-aqueous liquid chosen from a $C_1$ to $C_4$ alkanol, aldehyde or ketone or mixtures thereof with water;
    (ii) subsequently contacting the matrix with a second non-aqueous liquid which is miscible with the first and which has a dielectric constant which is lower than that of the first non-aqueous liquid;
    (iii) drying the matrix to remove superficial remains of liquid to provide a dry-to-the-touch article; and
    (iv) packaging the article in a closed moisture impervious container.

* * * * *